United States Patent
Daglow et al.

(10) Patent No.: US 8,315,714 B2
(45) Date of Patent: *Nov. 20, 2012

(54) BURR HOLE CAPS AND METHODS OF USE

(75) Inventors: Terry D. Daglow, Allen, TX (US); Timothy S. Jones, Carrollton, TX (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/239,108

(22) Filed: Sep. 21, 2011

(65) Prior Publication Data

US 2012/0010626 A1    Jan. 12, 2012

Related U.S. Application Data

(63) Continuation of application No. 12/020,229, filed on Jan. 25, 2008, now Pat. No. 8,050,772.

(60) Provisional application No. 60/886,614, filed on Jan. 25, 2007.

(51) Int. Cl.
*A61N 1/372* (2006.01)
*A61M 5/32* (2006.01)

(52) U.S. Cl. ........ 607/116; 607/115; 607/117; 607/139; 607/149; 604/174

(58) Field of Classification Search ............... 607/149, 607/115–117, 139
See application file for complete search history.

(56) References Cited

U.S. PATENT DOCUMENTS

| | | | |
|---|---|---|---|
| 4,245,645 A | 1/1981 | Arseneault et al. |
| 4,328,813 A | 5/1982 | Ray |
| 4,998,938 A | 3/1991 | Ghajar et al. |
| 5,464,446 A | 11/1995 | Dreesen et al. |
| 5,843,150 A | 12/1998 | Dreesen et al. |
| 5,865,842 A | 2/1999 | Knuth et al. |
| 5,927,277 A | 7/1999 | Baudino et al. |
| 5,954,687 A | 9/1999 | Baudino |
| 6,044,304 A | 3/2000 | Baudino |
| 6,134,477 A | 10/2000 | Knuteson |
| 6,210,417 B1 | 4/2001 | Baudino et al. |
| 6,482,182 B1 | 11/2002 | Carroll et al. |
| 7,454,251 B2 | 11/2008 | Rezai et al. |
| 2005/0015128 A1 | 1/2005 | Rezai et al. |
| 2010/0023100 A1 | 1/2010 | Barker |

*Primary Examiner* — Joseph Stoklosa
(74) *Attorney, Agent, or Firm* — Craig Hoersten; Christopher S. L. Crawford (57) ABSTRACT

In one embodiment, a kit, for securing a lead or cannula within a burr hole, comprises: a base structure to be positioned immediately adjacent to or partially within the burr hole; a lead securing member for securing the lead within the burr hole, the lead securing member comprising a first arm structure and a second arm structure, at least one spring loaded structure adapted to exert a force to bring the first arm structure and the second arm structure together; and a positioning tool having a distal end adapted to be inserted within the lead securing member; wherein when the distal end of the positioning tool is positioned within the lead securing member, the distal end holds the first and second arm structures a sufficient distance apart to receive a lead or a cannula between the first and second arm structures.

20 Claims, 8 Drawing Sheets

BURR HOLE CAPS AND METHODS OF USE

CROSS-REFERENCE TO RELATED APPLICATION(S)

This application is a continuation of U.S. application Ser. No. 12/020,229, filed Jan. 25, 2008, now U.S. Pat. No. 8,050,772, which claims the benefit of U.S. Provisional Application No. 60/886,614, filed Jan. 25, 2007, which is incorporated herein by reference.

BACKGROUND

Deep brain stimulation (DBS) refers to the delivery of electrical pulses into one or several specific sites within the brain of a patient to treat various disorders. For example, DBS has been proposed as a clinical technique for treatment of chronic pain, essential tremor, Parkinson's disease (PD), dystonia, epilepsy, depression, obsessive-compulsive disorder, and other disorders.

A DBS procedure typically involves first obtaining preoperative images of the patient's brain (e.g., using computer tomography (CT) or magnetic resonance imaging (MRI)). The imaging process sometimes involves first affixing to the patient's skull fiducial markers that are discernable on the images produced by the imaging process. The fiducial markers assist in registering the preoperative images to the actual physical position of the patient in the operating room during the subsequent surgical procedure. Using the preoperative images, the neurosurgeon can select a target region within the brain, an entry point on the patient's skull, and a desired trajectory between the entry point and the target region. The entry point and trajectory are carefully selected to avoid intersecting or otherwise damaging critical brain structures.

In the operating room, the patient is immobilized and the patient's actual physical position is registered. The physician marks the entry point on the patient's skull and drills a burr hole at that location. A mechanism is provided to precisely control the path through the patient's brain to the desired location. Specifically, a positioning error on the order of a millimeter can have a significant negative effect on the efficacy of the DBS therapy. Stereotactic instrumentation and trajectory guide devices are commercially available products that facilitate the control of the trajectory and positioning of a lead during the surgical procedure.

A microdrive introducer can be used to insert a deep brain stimulation lead toward the selected region of the brain along the selected trajectory. The lead provides one or several conductive paths to deliver stimulation pulses to the selected region. The lead includes a very small diameter insulative lead body with one or several conductors (e.g., stranded wires) embedded in the insulative material. The lead also includes one or several electrodes at a distal end of the lead that are electrically coupled to respective conductors. The electrodes can be used to record signals within the brain and/or to deliver electrical stimulation pulses to brain tissue. Often, the electrical activity adjacent to one or several electrodes is analyzed to determine whether the recorded signals are consistent with the targeted region of the brain. If the recorded signals are not consistent with the targeted region, an adjustment to the lead's position can be made as appropriate.

A burr hole plug or cap structure is typically utilized to retain the lead in the desired position. A burr hole structure generally includes: (i) a ring or grommet-like element that is inserted into the hole first so as to protect the edges of the burr hole and (ii) a cap or plug device that is inserted into the ring or grommet-like element to secure the lead and plug the hole.

By way of example, in U.S. Pat. No. 6,044,304, a burr ring is disclosed that is secured to the skull. The burr hole plug of the '304 patent also has an upper flange portion and circumferential ribs used to position the plug in the cranium. Also, the burr hole plug described in the '304 patent includes an aperture capable of accepting a lead through a septum.

In U.S. Pat. No. 5,954,687, a device is disclosed for securing a catheter within a burr hole. The device has a series of spaced septum elements that can be selectively penetrated for fluid communication with a reservoir in the apparatus. The main objective of the device is to allow fluid access to the patient's brain through a burr hole. Anchoring of the device is not taught and there are a limited predetermined number of septum holes that can be accessed.

U.S. Pat. No. 5,927,277 describes a burr hole ring for retaining a probe relative to the skull. The burr hole ring has an engaging member with holes to receive a probe. The '277 patent also describes a method for securing a device at a desired orientation within the burr hole. Since a fixed spacing between holes is described, the device can be placed in a limited number of locations through the burr hole.

U.S. Pat. No. 5,865,842 discloses a system and method for anchoring a lead in a burr hole. The disclosed system consists of a base-plate, adaptor, seal, and screw cap. The lead is anchored mechanically at the burr hole at a 90 degree angle relative to the burr hole.

U.S. Pat. No. 5,843,150 discloses an annular clamping means with a compressible feed-through member for receiving a lead. The described order for anchoring the lead includes making the burr hole, inserting the plug ring, inserting the lead, and engaging the clamping member.

Other burr hole plug assemblies and features of burr hole plugs are taught in U.S. Pat. No. 5,464,446 (burr hole plug with a central lumen and a cap that engages with the flange of the plug); U.S. Pat. No. 4,998,938 (a device that facilitates insertion of an instrument into a patient's cranial cavity); U.S. Pat. No. 4,328,813 (a burr hole plug with a cap that anchors the lead); and U.S. Pat. No. 4,245,645 (a probe and system that is used to perform stereoelectroencephalographic exploration).

SUMMARY

In one embodiment, a kit, for securing a lead or cannula within a burr hole, comprises: a base structure to be positioned immediately adjacent to or partially within the burr hole; a lead securing member for securing the lead within the burr hole, the lead securing member comprising a first arm structure and a second arm structure, at least one spring loaded structure adapted to exert a force to bring the first arm structure and the second arm structure together; and a positioning tool having a distal end adapted to be inserted within the lead securing member; wherein when the distal end of the positioning tool is positioned within the lead securing member, the distal end holds the first and second arm structures a sufficient distance apart to receive a lead or a cannula between the first and second arm structures.

The foregoing has outlined rather broadly certain features and/or technical advantages in order that the detailed description that follows may be better understood. Additional features and/or advantages will be described hereinafter which form the subject of the claims. It should be appreciated by those skilled in the art that the conception and specific embodiment disclosed may be readily utilized as a basis for modifying or designing other structures for carrying out the same purposes. It should also be realized by those skilled in the art that such equivalent constructions do not depart from the spirit and scope of the appended claims. The novel features, both as to organization and method of operation, together with further objects and advantages will be better understood from the following description when considered in connection with the accompanying figures. It is to be expressly understood, however, that each of the figures is provided for the purpose of illustration and description only and is not intended as a definition of the limits of the appended claims.

DETAILED DESCRIPTION

Although a number of burr hole devices have been made commercially available, many burr hole cap devices suffer from various limitations. For example, some commercially available burr hole devices are too simple in design and do not provide adequate stabilization of the lead with the burr hole. Alternatively, other commercially available burr hole devices that achieve the desired stabilization of the lead within the burr hole are quite cumbersome during the placement and manipulation to capture the lead within the burr hole. Specifically, burr holes are relatively small, e.g., about 14 mm. Accordingly, the individual elements of a burr hole device can be quite small. Thus, when burr hole devices require precise manipulations, the lead securing process can be quite tedious. In contrast, representative embodiments provide burr hole devices that provide a desired amount of stabilization of the lead without requiring undue and cumbersome manipulation of small constituent elements.

Figure 1:
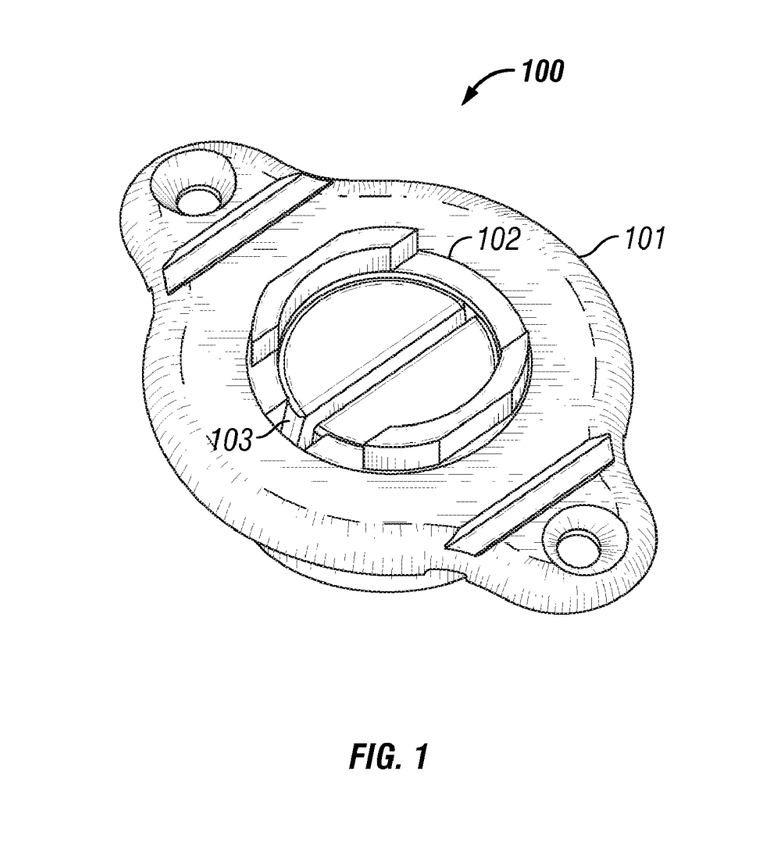
FIG. 1 depicts a burr hole assembly according to one representative embodiment.

FIG. 1 depicts burr hole 100 assembly according to one representative embodiment. For the sake of clarity, the actual cap for the burr hole assembly is omitted to enable the interior details of assembly 100 to be shown in FIG. 1. As shown in FIG. 1, burr hole cap assembly comprises 100 outer ring 101, wedge member 102, and grasping member 103.

Figure 2:
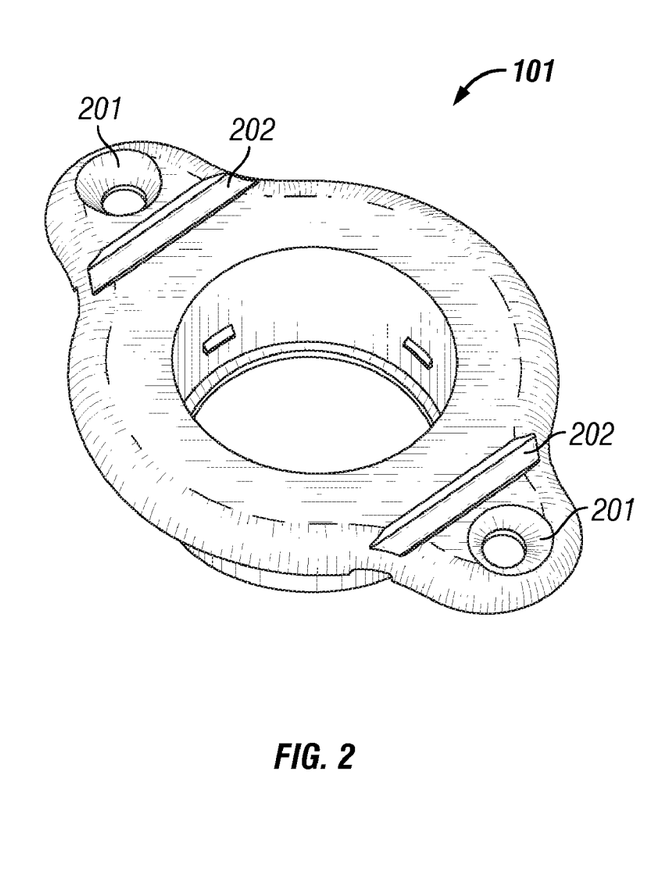
FIG. 2 depicts an outer ring adapted to be placed within the burr hole of the patient.

In one embodiment as shown in FIG. 2, outer ring 101 is adapted to be placed within the burr hole of the patient. Outer ring 101 possesses a small profile somewhat flat portion that is intended to remain on the patient's skull and an annular portion adapted to be inserted within the burr hole. Additionally, outer ring 101 is preferably fabricated from a bio-stable, bio-compatible polymer material. Outer ring 101 preferably possesses some amount of rigidity and strength to promote mechanical robustness and stability. Outer ring 101 includes apertures 201 for receiving bone screws to secure outer ring 101 to the patient's skull after outer ring 101 has been placed with the burr hole. In the embodiment shown in FIG. 2, outer ring 101 comprises securing members 202 into which a cap structure (not shown) can be coupled.

Figure 3:
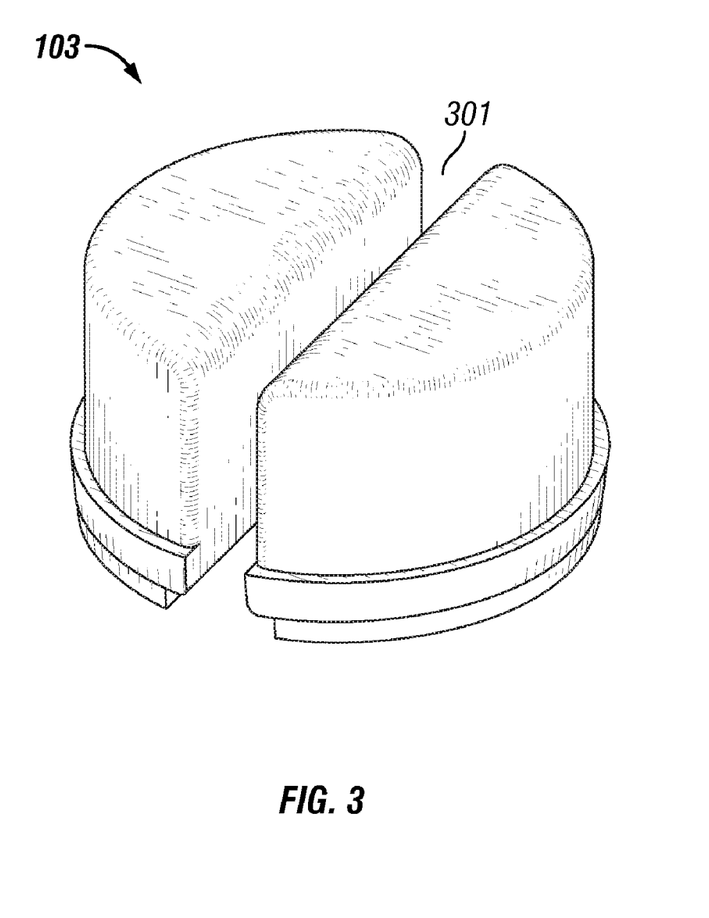
FIG. 3 depicts a grasping member adapted to fit around the lead.

In one embodiment as shown in FIG. 3, grasping member 103 is adapted to fit around the lead and to be placed within the outer ring 101 with relatively little difficulty. As shown in FIG. 3, grasping member 103 is a somewhat annular structure. Grasping member 103 could alternatively be tapered or possess a truncated cone-shape to facilitate the assembly of burr hole cap assembly 100. Grasping structure 301 comprises gap 301 that runs along a substantial portion of the diameter of grasping member 103. Preferably, grasping member 103 is a single integral structure and gap 301 is only completely open on only one side of grasping member 103. Additionally, grasping member 103 is preferably fabricated of a bio-compatible and bio-stable material that possesses a relatively low durometer to cause grasping member 103 to be compressible. For example, grasping member 103 can be fabricated from a suitable silicone material.

In use, when a lead is positioned within the burr hole of a patient, grasping member 103 is placed around the lead using gap 301. When grasping member 103 is not compressed, gap 301 possesses a width that is sufficiently greater than the diameter of the lead to prevent application of an excessive frictional force on the lead. Thus, grasping member 103 can be placed on the lead at a distance away from the position where outer ring 101 is secured to the skull. Then, grasping member 103 can be slid along the lead and into the outer ring without dislocating the lead within the patient. The outside diameter of grasping member 103 is preferably smaller that the inside diameter of outer ring 101 thereby allowing the insertion of grasping member 103 into outer ring 101 to occur with little complication.

Figure 4:
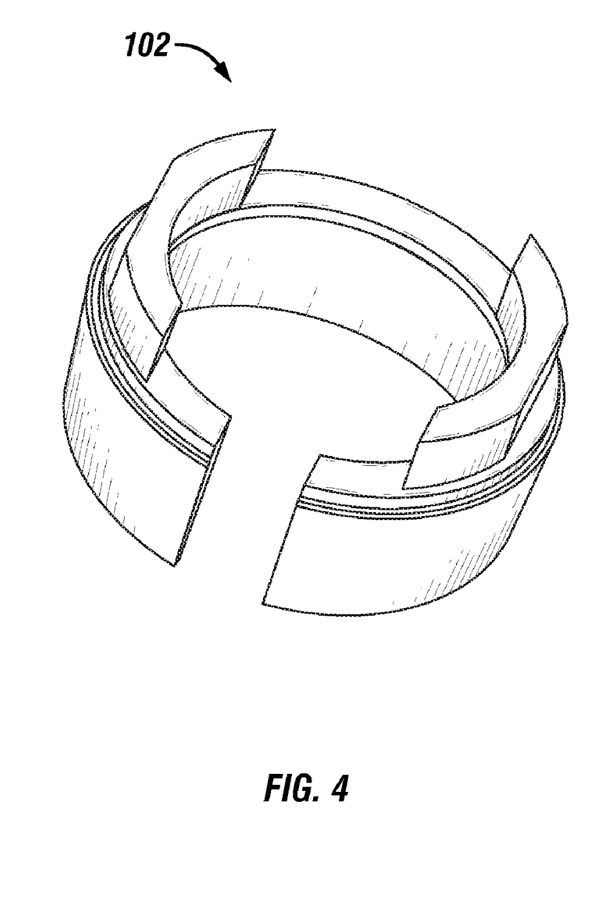
FIG. 4 depicts an outer ring adapted for the grasping member of FIG. 3.

After grasping member 103 is placed around the lead and within outer ring 101, wedge member 102 (as shown in isolation in FIG. 4) is placed around grasping member 103 and within outer ring 101 to form the assembly shown in FIG. 1. Wedge member 102 preferably possesses a durometer that is greater than the durometer of grasping member 103. Additionally, wedge member 102 preferably possesses an inner diameter that is smaller than the outside diameter of grasping member 103. Accordingly, when wedge member 102 is placed around grasping member 103, wedge member 102 compresses grasping member 103 thereby narrowing gap 301 and securing the lead.

Figure 5:
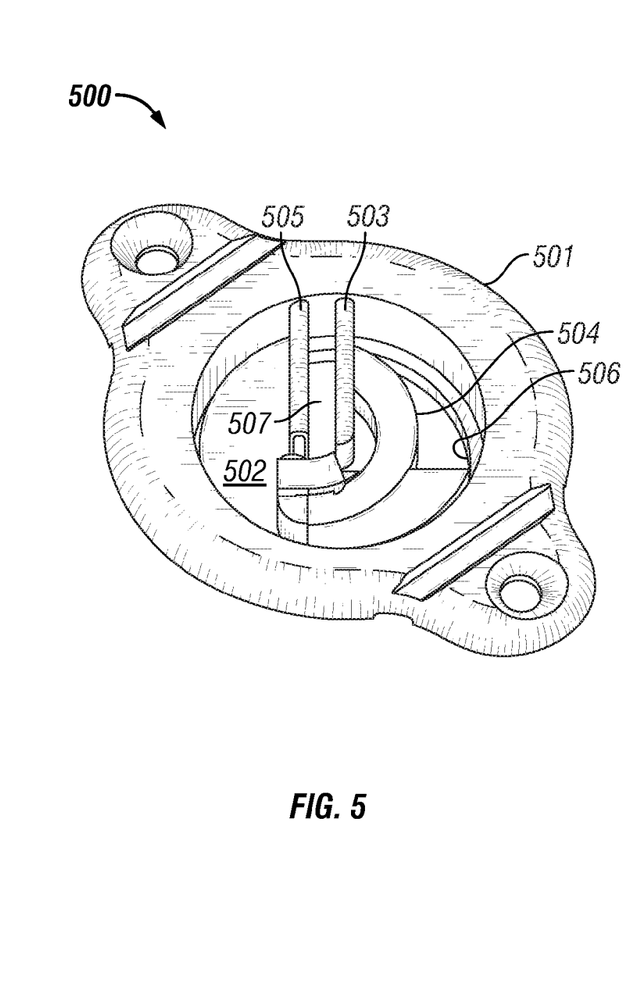
FIG. 5 depicts another burr hole assembly.

FIG. 5 depicts another burr hole device that enables a lead to be secured within a burr hole with a relatively minimal amount of difficulty. As shown in FIG. 5, burr hole device 500 includes outer ring 501 which is preferably implemented in a manner similar to outer ring 101. Inner disc 502 is adapted to be placed within outer ring 501 and around the lead. Preferably, outer ring 501 possesses interior flange or edge 506 to hold inner disc 502. Also, inner disc 502 is preferably rotatable within outer ring 501 to enable the lead to be captured from substantially any position within the burr hole. Inner disc 502 preferably comprises a first arm structure 505 that is rigidly fixed on inner disc 502. Second arm structure 503 is preferably attached to moveable curved projection element 504 which thereby allows a "window" 507 of space through burr hole device 500 to be opened and closed.

In use, with second arm structure 503 positioned such that window 507 is as wide as possible, inner disc 502 is placed within outer ring 501 such that the lead is positioned between arms 503 and 505. Inner disc 502 is then rotated within outer ring 501 by pushing a suitable tool against rigid arm 505 until rigid arm 505 is positioned against the lead. By implementing rigid arm 505 to protrude above the main surface of inner disc 502, rigid arm 505 can be used to rotate disc 502 within ring 501. Thereby, the manipulation of disc 502 into the correct position can occur in an efficient manner and cumbersome precision movements are not required. Then, arm 503 is rotated toward arm 505 to secure the lead between arms 503 and 505.

Figure 6:
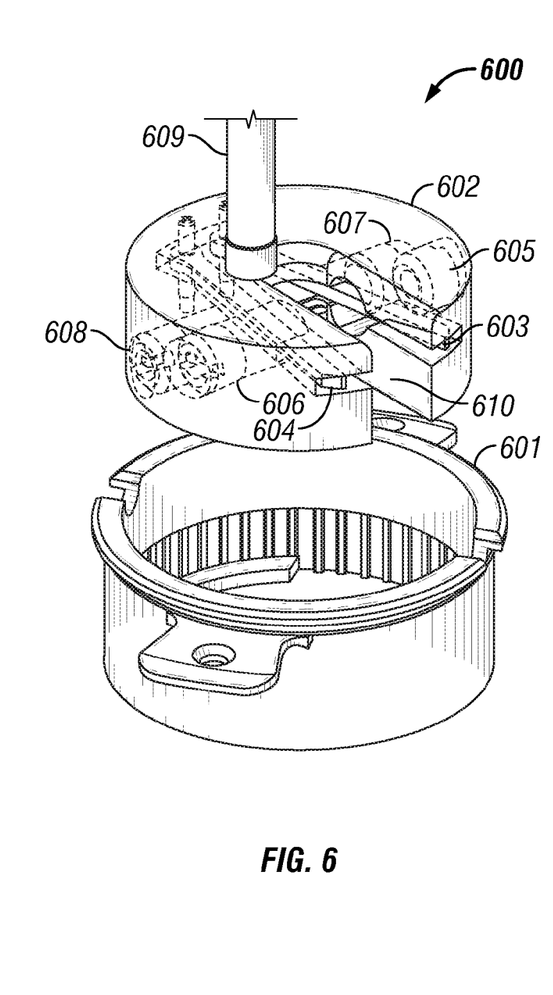
FIG. 6 depicts a burr hole assembly and grasping tool according to one representative embodiment.

FIG. 6 depicts burr hole device 600 according to another embodiment. Burr hole device 600 is similar to burr hole device 500 in that the lead is secured between arms 603 and 604. Burr hole device 600 differs from burr hole device 500 in the manner in which arms 603 and 604 are brought together to secure the lead.

As shown in FIG. 6, burr hole device 600 comprises annular structure 601 that is inserted within the burr hole of the patient and secured to the patient's skull. On the interior wall of annular structure 601, a lower flange or edge can be provided to hold lead securing member 602. Also, annular structure 601 may comprise ridges or other structures on its interior wall to limit the rotation of lead securing member 602.

In use, tool 609 is initially inserted within lead securing member 602. Upper lever structures 605 and 606 (e.g., "dead bolts") are spring loaded such that lever structures 605 and 606 exert an "inward" force against arms 603 and 604, respectively. Although spring loaded lever structures are shown for one embodiment, other shape memory elements could be employed. For example, suitably shaped wire elements having spring characteristics could be employed in lieu of spring loaded lever structures. When the distal end of tool 609 is inserted within lead securing member 602, arms 603 and 604 clamp against the distal end of tool 609 as shown in FIG. 6. The distal end of tool 609 maintains an opening 610 (between arms 603 and 604) large enough to accept the lead with or without a cannula with little difficulty. Also, the clamping force applied by arms 603 and 604 against tool 609 allows lead securing member 602 to be moved and manipulated into place by using tool 609 (see FIG. 7). Additionally, when inserted within lead securing member 602, the distal end of tool 609 maintains spring loaded lever structures 607 and 608 in a "closed" position. That is, lever structures 607 and 608 are spring loaded to automatically open and contact an inner shoulder of annular structure 601 when the distal end of tool 609 is removed. The expansion or opening of lever structures 607 and 608 causes securing member 602 to be secured within annular structure 601.

Figure 7:
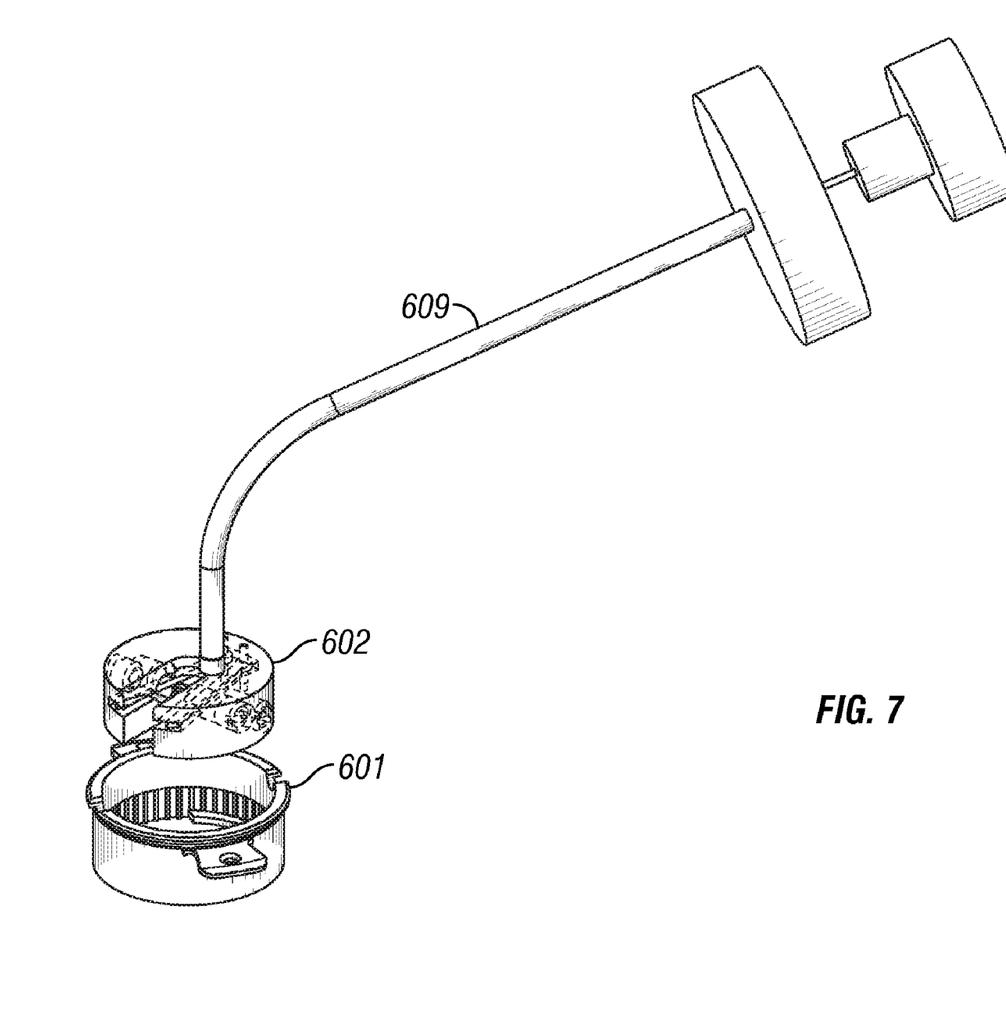
FIG. 7 depicts an another view of the burr hole assembly and grasping tool shown in FIG. 6 according to one representative embodiment.

FIG. 7 depicts an expanded view of tool 609 inserted within securing member 602. As shown, a surgeon can grasp tool 609 to pick-up and move securing member 602 for placement within annular structure 601 with relative ease. Once, lead securing member 602 is positioned around the lead and within the annular structure, the surgeon need only remove tool 609 from lead securing member 602 to secure the lead and lock member 602 into place against annular structure 601. Specifically, as the distal end of tool 609 is removed, arms 603 and 604 clamp around the lead (or the cannula) due to the application of force exerted by spring loaded lever structures 605 and 606. Also, as tool 609 is removed, spring load lever structures 607 and 608 expand to contact annular structure 601.

Figure 8:
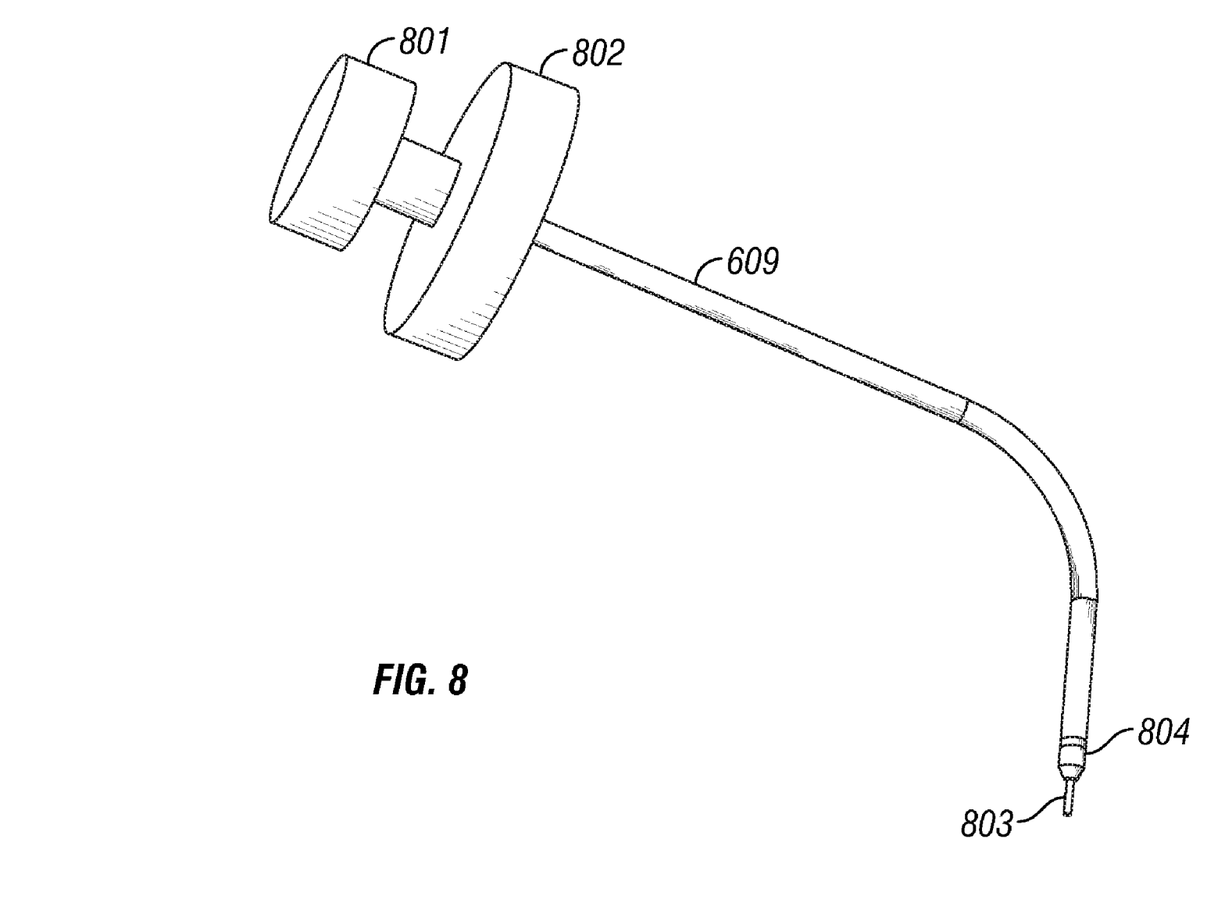
FIG. 8 depicts a grasping tool is isolation according to one representative embodiment.

FIG. 8 depicts another view of tool 609. As shown in FIG. 8, tool 609 comprises handles 801 and 802 at is proximal end. When handles 801 and 802 are compressed together, pin 803 is extended from the distal end of 609. Pin 803 is used to remove the distal end of tool 609 from annular structure 601. Specifically, when extended, pin 803 contacts an interior surface of annular structure 601 thereby pushing end 804 of tool 609 upward. When end 804 is pushed upward, arms 603 and 604 are no longer held apart by end 804 and arms 603 and 604 contract toward each other to clamp around the lead. Additionally, end 804 is tapered to allow end 804 to be re-inserted within annular structure 601 to push arms 603 and 604 apart and to retract lever structures 607 and 608. Accordingly, lead securing member 602 can be removed from annular structure 601 as efficiently as it can be inserted with structure 601.

Figure 9:
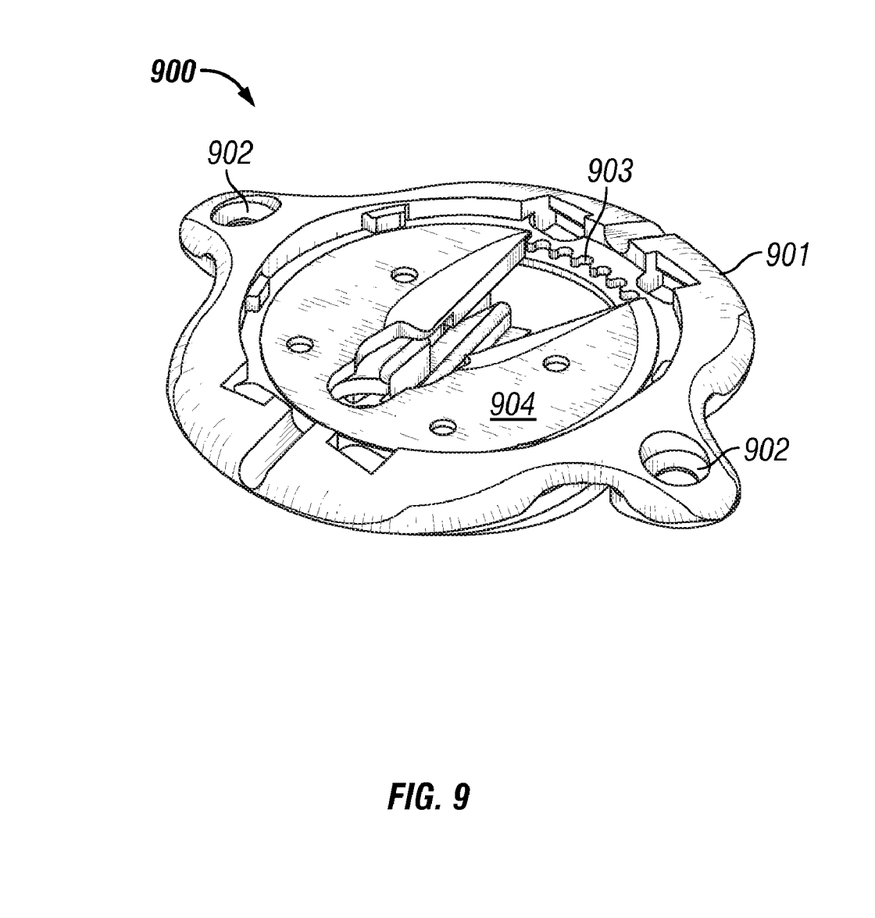
FIGS. 9, 10A, 10B, and 11-13 depict respective portions of a burr hole device according to another representative embodiment.

FIG. 9 depicts an assembled view of burr hole cap 900 according to another representative embodiment. Burr hole cap 900 is preferably assembled from a plurality of components including annular structure 901. Annular structure 901 is preferably adapted to be inserted within the burr hole of the patient and secured to the patient's skull. For example, suitable bone screws could be placed into the patient's skull through apertures 902. As shown in FIG. 9, annular structure 901 preferably comprises ridges or teeth 903 or other similar structures along its interior circumference to limit the rotation of lead securing member 904.

Figure 10A:
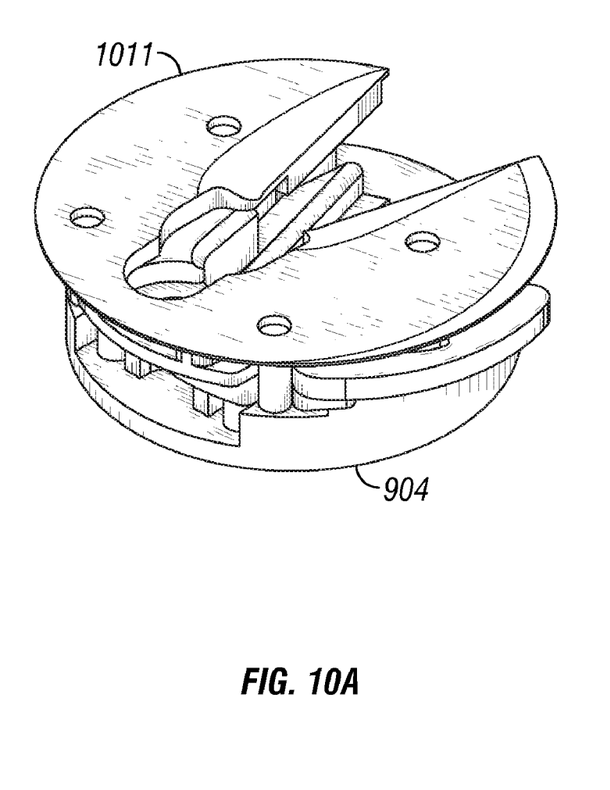
Figure 10B:
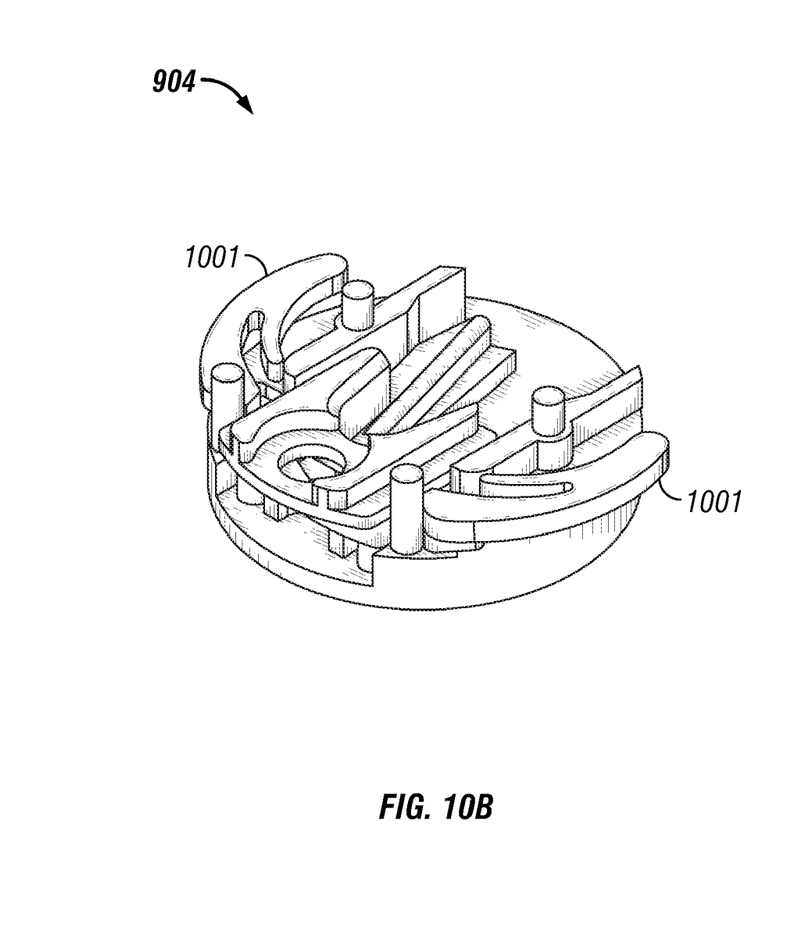

Lead securing member 904 is shown individually in FIG. 10A. Lead securing member 904 comprises plate structure 1011 which is preferably adapted to mate with annular structure 901. For example, plate structure 1011 may comprise a plurality of ridges (preferably underneath the upper surface and, hence, not shown in FIG. 10A) to fit within ridges 903 of annular structure 901. FIG. 10B shows lead securing member 904 without plate structure 1011 to more clearly depict other components of lead securing member 904.

Figure 11:
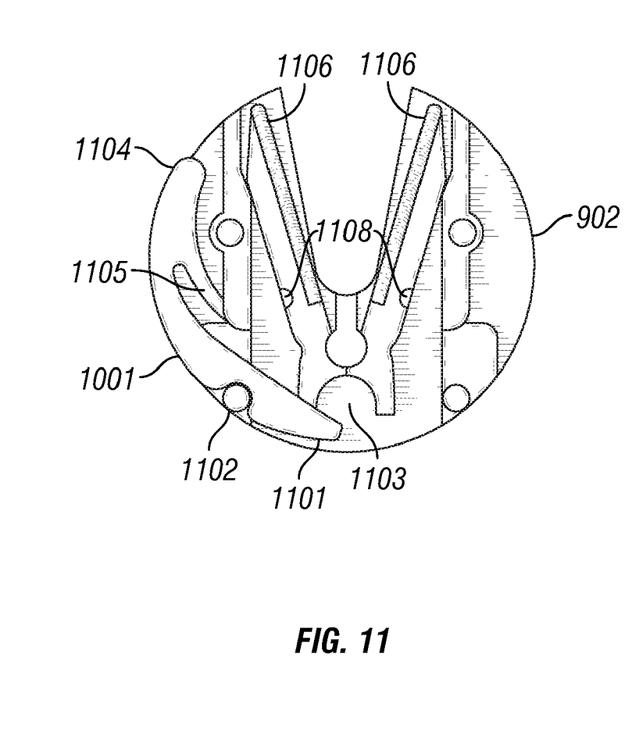
Figure 13:
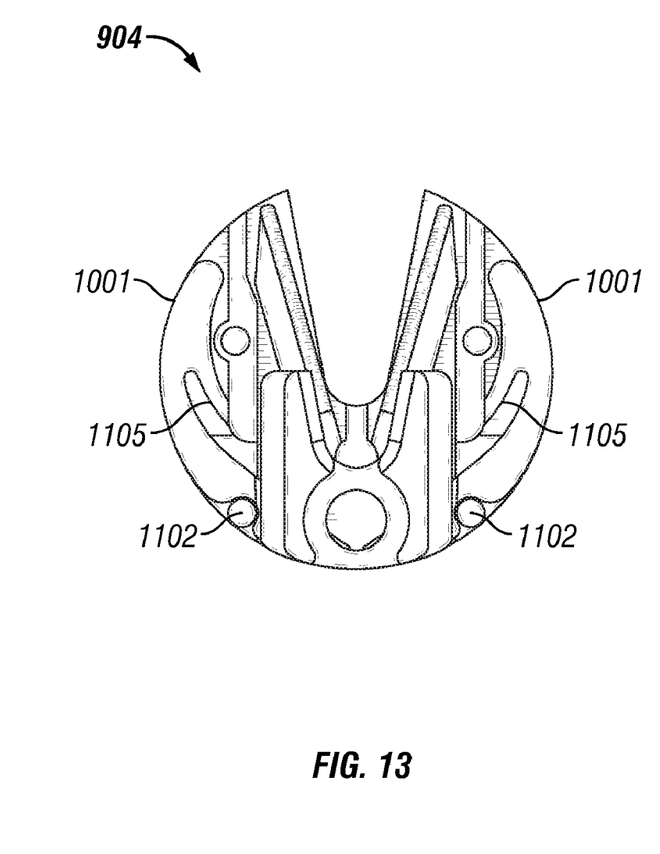

Lead securing member 904 preferably comprises a plurality of "wing" structures 1001. Preferably, wing structures 1001 possess a spring characteristic (e.g., from their material characteristics). As shown in FIG. 10B, when not compressed, wing structures 1001 tend to expand beyond the perimeter of the remainder of lead securing member 904. As shown more clearly in FIG. 11, each wing structure 1001 is preferably pivotally disposed about pin 1102. When a suitable force is applied to end 1101 of wing structure 1001 (e.g., by insertion of a suitable tool into aperture 1103), wing structure 1001 is forced to pivot and end 1104 of wing structure 1001 is moved inward. Wing structure 1001 is then preferably aligned with the circumference of lead securing member 904 (see FIG. 13) and spring elements 1105 are compressed.

Figure 12:
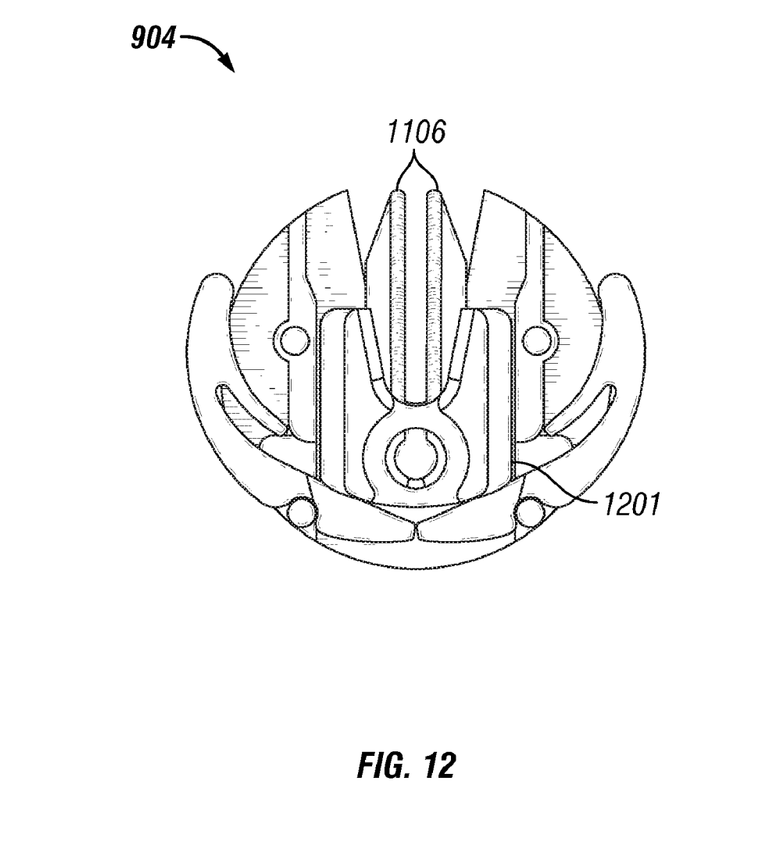

When wing structures 1001 are suitably retracted in this manner, lead securing member 904 is placed within annular structure 901. The ridges or teeth 903 of annular structure 901 interlock with the corresponding ridges or teeth of plate structure 1011 thereby limiting the rotation of lead securing member 904. The placement tool is subsequently removed from aperture 1103 and spring elements 1105 apply an expansive force to wing structures 1001. In response to the applied force by spring elements 1105, wing structures 1001 press against the inner surface of annular structure 901 thereby locking lead securing member 904 in place. When it is desired to lock the stimulation lead or the cannula into place, slider structure 1201 is moved forward as shown in FIG. 12. As slider structure 1201 is advanced, slider structure 1201 brings grasping members 1106 together and thereby contact the lead or cannula. Preferably, slider structure 1201 is adapted to lock into place when a suitable structure of slider 1201 "snaps" into indentations 1108 (see FIG. 11) on grasping structures 1106.

Although representative embodiments and advantages have been described in detail, it should be understood that various changes, substitutions and alterations can be made herein without departing from the spirit and scope of the appended claims. Moreover, the scope of the present application is not intended to be limited to the particular embodiments of the process, machine, manufacture, composition of matter, means, methods and steps described in the specification. As one of ordinary skill in the art will readily appreciate from this disclosure, processes, machines, manufacture, compositions of matter, means, methods, or steps, presently existing or later to be developed that perform substantially the same function or achieve substantially the same result as the corresponding embodiments described herein may be utilized without departing from the scope of the appended claims. Accordingly, the appended claims are intended to include within their scope such processes, machines, manufacture, compositions of matter, means, methods, or steps.

What is claimed:

1. A kit for securing a lead or cannula within a burr hole, comprising:
    a base structure to be positioned immediately adjacent to or partially within the burr hole;
    a lead securing member for securing the lead within the burr hole, the lead securing member comprising first arm structure having first edge and a second arm structure having a second edge, the first arm structure and second arm structure being movable between a first position and a second position such that when in the first position the first edge and the second edge are substantially parallel and when in the second position the first edge and the second edge are non-parallel;
    the lead securing member including at least one spring loaded structure adapted to exert a force to bias the first arm structure and the second arm structure in the first position; and
    a positioning tool having a distal end adapted to be inserted within the lead securing member;
    wherein when the distal end of the positioning tool is positioned within the lead securing member, the distal end moves the first and second arm structures to the second position and a sufficient distance apart to receive a lead or a cannula between the first and second arm structures;
    wherein the positioning tool comprises a control structure at a proximal end that, when engaged, causes the distal end of the positioning tool to be released from the lead securing member allowing the first and second arm structures move towards the first position to secure the lead or cannula between the first edge and the second edge.

2. The kit of claim 1 wherein the lead securing member comprises at least one other spring loaded structure that expands upon removal of the distal end of the positioning tool to cause a locking member of the lead securing member to contact with the base structure.

3. The kit of claim 1 wherein the lead securing member comprises a substantially annular cover that covers a substantial portion of the burr hole.

4. The kit of claim 1 wherein the at least one spring loaded structure is adapted to apply force to a plurality of wing structures, each of the plurality of wing structures disposed to pivot about respective pin elements.

5. The kit of claim 4 wherein the plurality of wing structures are disposed on perimeter portions of the lead securing member.

6. The kit of claim 4 wherein the lead securing member further comprises:
    a slider structure that is adapted to slide along a direction that is substantially longitudinal relative to the first and second arm structures, wherein when the slider structure is advanced, the slider structure brings the first and second arm structures towards the first position to secure the lead or cannula, wherein the plurality of wing structures contact the slider structure.

7. The kit of claim 6 wherein the first and second arm structures are adapted to snap-lock with the slider structure in a position where the lead or cannula is secured.

8. The kit of claim 4 wherein the at least one spring loaded structure comprises a plurality of extension structures, the plurality of extension structures are attached to the plurality of wing structures, and the extension structures flexibly impinge on wall structures of the lead securing member.

9. The kit of claim 1 wherein the first and second arm structures form an inner surface to receive the distal end of the positioning tool.

10. The kit of claim 1 wherein the base structure and the lead securing member comprise respective opposing irregular surfaces adapted to prevent rotation of the lead securing member within the base structure.

11. A burr hole cap for securing a lead or cannula within a burr hole, comprising:
    a base structure to be positioned immediately adjacent to or partially within the burr hole;
    a lead securing member for securing the lead within the burr hole, the lead securing member comprising first arm structure having first edge and a second arm structure having a second edge, the first arm structure and second arm structure being movable between a first position and a second position such that when in the first position the first edge and the second edge are substantially parallel and when in the second position the first edge and the second edge are non-parallel;
    the lead securing member including at least one spring loaded structure adapted to exert a force to bias the first arm structure and the second arm structure in the first position; and
    wherein when a positioning tool is positioned within the lead securing member, the positioning tool moves the first and second arm structures to the second position and a sufficient distance apart to receive a lead or a cannula between the first and second arm structures;
    wherein when the positioning tool is removed from the lead securing member the first and second arm structures move towards the first position to secure the lead or cannula between the first edge and the second edge.

12. The burr hole cap of claim 11 wherein the lead securing member comprises at least one other spring loaded structure that expands upon removal of the positioning tool to cause a locking member of the lead securing member to contact with the base structure.

13. The burr hole cap of claim 11 wherein the lead securing member comprises a substantially annular cover that covers a substantial portion of the burr hole.

14. The burr hole cap of claim 11 wherein the at least one spring loaded structure is adapted to apply force to a plurality of wing structures, each of the plurality of wing structures disposed to pivot about respective pin elements.

15. The burr hole cap of claim 14 wherein the plurality of wing structures are disposed on perimeter portions of the lead securing member.

16. The burr hole cap of claim 14 wherein the lead securing member further comprises:
    a slider structure that is adapted to slide along a direction that is substantially longitudinal relative to the first and second arm structures, wherein when the slider structure is advanced, the slider structure brings the first and second arm structures towards the first position to secure the lead or cannula, wherein the plurality of wing structures contact the slider structure.

17. The burr hole cap of claim 16 wherein the first and second arm structures are adapted to snap-lock with the slider structure in a position where the lead or cannula is secured.

18. The burr hole cap of claim 14 wherein the at least one spring loaded structure comprises a plurality of extension structures, the plurality of extension structures are attached to the plurality of wing structures, and the extension structures flexibly impinge on wall structures of the lead securing member.

19. The burr hole cap of claim 11 wherein the first and second arm structures form an inner surface to receive the distal end of the positioning tool.

20. The burr hole cap of claim 11 wherein the base structure and the lead securing member comprise respective opposing irregular surfaces adapted to prevent rotation of the lead securing member within the base structure.

* * * * *